United States Patent
Tischler et al.

(10) Patent No.: US 8,211,162 B2
(45) Date of Patent: Jul. 3, 2012

(54) CONNECTOR NODE FOR DURABLE STENT

(75) Inventors: Brian Tischler, New Brighton, MN (US); Chad Perrin, Coon Rapids, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1011 days.

(21) Appl. No.: 11/753,829

(22) Filed: May 25, 2007

(65) Prior Publication Data

US 2008/0294238 A1 Nov. 27, 2008

(51) Int. Cl.
*A61F 2/06* (2006.01)

(52) U.S. Cl. ................................................ 623/1.15

(58) Field of Classification Search .............. 623/1.15, 623/1.12, 1.13, 1.16, 1.17, 1.18, 1.19, 1.2
See application file for complete search history.

(56) References Cited

U.S. PATENT DOCUMENTS

| | | | |
|---|---|---|---|
| 5,195,969 A | 3/1993 | Wang et al. | |
| 5,270,086 A | 12/1993 | Hamlin | |
| 5,366,504 A | 11/1994 | Anderson et al. | |
| 5,674,242 A | 10/1997 | Phan et al. | |
| 5,733,303 A * | 3/1998 | Israel et al. | 623/1.15 |
| 5,780,807 A | 7/1998 | Saunders | |
| 5,807,404 A | 9/1998 | Richter | |
| 5,876,449 A | 3/1999 | Starck et al. | |
| 5,922,020 A * | 7/1999 | Klein et al. | 623/1.15 |
| 6,001,123 A | 12/1999 | Lau | |
| 6,042,606 A | 3/2000 | Frantzen | |
| 6,190,406 B1 | 2/2001 | Duerig et al. | |
| 6,203,569 B1 | 3/2001 | Wijay | |
| 6,264,687 B1 | 7/2001 | Tomonto | |
| 6,273,911 B1 | 8/2001 | Cox et al. | 623/1.15 |
| 6,312,460 B2 | 11/2001 | Drasler et al. | 623/1.15 |
| 6,409,754 B1 | 6/2002 | Smith et al. | |
| 6,451,052 B1 | 9/2002 | Burmeister et al. | |

(Continued)

FOREIGN PATENT DOCUMENTS

EP 0734698 10/1996

(Continued)

OTHER PUBLICATIONS

Schetsky, L. McDonald, "Shape Memory Alloys", Encyclopedia of Chemical Technology (3rd ed.), John Wiley & Sons, 1982, vol. 20. pp. 726-736.

*Primary Examiner* — Ryan Severson
*Assistant Examiner* — Jonathan W Miles
(74) *Attorney, Agent, or Firm* — Vidas, Arrett and Steinkraus (57) ABSTRACT

A stent has adjacent bands being connected by connectors. Each band has a plurality of interconnected struts. The width of a portion of a strut end region is greater than the width of a portion of the strut medial region. Adjacent strut end regions within a band are connected at a turn. Each connector has first and second connector end regions, and a connector medial region. The width of a portion of the first connector end region or second connector end region is greater than the width of a portion of the connector medial region. The first connector end region is engaged to one turn of a first band and the second connector end region is engaged to one turn of a second longitudinally adjacent band, the first and second bands having connected turns and unconnected turns, the connected turns having a greater width than the unconnected turns.

14 Claims, 7 Drawing Sheets

U.S. PATENT DOCUMENTS

| | | |
|---|---|---|
| 6,485,507 B1 | 11/2002 | Walak et al. |
| 6,533,807 B2 | 3/2003 | Wolinsky et al. ............ 623/1.15 |
| 6,540,774 B1 | 4/2003 | Cox |
| 6,565,599 B1 * | 5/2003 | Hong et al. .................. 623/1.15 |
| 6,613,079 B1 | 9/2003 | Wolinsky et al. ............ 623/1.15 |
| 6,676,987 B2 | 1/2004 | Zhong et al. |
| 6,699,278 B2 | 3/2004 | Fischell et al. ............... 623/1.15 |
| 6,726,712 B1 | 4/2004 | Raeder-Deven et al. |
| 6,764,505 B1 | 7/2004 | Hossainy et al. ............ 623/1.15 |
| 6,764,507 B2 | 7/2004 | Shanley et al. .............. 623/1.16 |
| 6,818,014 B2 | 11/2004 | Brown et al. |
| 6,852,124 B2 | 2/2005 | Cox et al. ..................... 623/1.15 |
| 6,896,696 B2 | 5/2005 | Doran et al. |
| 6,945,993 B2 | 9/2005 | Kveen et al. ................. 623/1.15 |
| 6,981,985 B2 | 1/2006 | Brown et al. ................. 623/1.15 |
| 7,147,660 B2 | 12/2006 | Chobotov et al. |
| 7,169,174 B2 | 1/2007 | Fischell et al. ............... 623/1.15 |
| 7,204,848 B1 | 4/2007 | Brown et al. |
| 7,344,560 B2 | 3/2008 | Gregorich et al. |
| 2002/0082681 A1 | 6/2002 | Boylan et al. |
| 2002/0144757 A1 | 10/2002 | Craig et al. |
| 2003/0004567 A1 | 1/2003 | Boyle et al. |
| 2003/0018380 A1 | 1/2003 | Craig et al. |
| 2003/0055485 A1 * | 3/2003 | Lee et al. ..................... 623/1.15 |
| 2003/0077200 A1 | 4/2003 | Craig et al. |
| 2003/0185895 A1 | 10/2003 | Lanphere et al. |
| 2004/0073291 A1 | 4/2004 | Brown et al. ................ 623/1.15 |
| 2004/0143317 A1 | 7/2004 | Stinson et al. |
| 2005/0049680 A1 * | 3/2005 | Fischell et al. ............... 623/1.15 |
| 2006/0224231 A1 | 10/2006 | Gregorich |
| 2007/0073384 A1 | 3/2007 | Brown et al. |

FOREIGN PATENT DOCUMENTS

| | | |
|---|---|---|
| EP | 0888757 A1 | 1/1999 |
| EP | 1767240 A1 | 3/2007 |
| WO | 9629028 | 9/1996 |
| WO | 9704721 | 2/1997 |
| WO | 9818407 | 5/1998 |
| WO | 9916387 | 4/1999 |
| WO | 0224111 | 3/2002 |
| WO | 2004058104 | 7/2004 |

* cited by examiner

CONNECTOR NODE FOR DURABLE STENT

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

In some embodiments this invention relates to implantable medical devices, their manufacture, and methods of use. More specifically, some embodiments of the present invention relate to stents.

2. Description of the Related Art

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents and similar devices such as stent, stent-grafts, expandable frameworks, and similar implantable medical devices, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. They may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All U.S. patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided to comply with 37 C.F.R. §1.72.

BRIEF SUMMARY OF THE INVENTION

In at least one embodiment, the invention is directed to a stent having a plurality of longitudinally adjacent bands, the longitudinally adjacent bands being connected by a plurality of connectors. Each band comprises a plurality of interconnected struts, each strut having a strut width, opposing strut end regions, and a strut medial region. The width of at least a portion of a strut end region is greater than the width of at least a portion of the strut medial region. Within a band, each strut end region is connected to an adjacent strut end region at a turn, each turn having a turn width. Each connector has a connector width, a first connector end region, a second connector end region, and a connector medial region therebetween. The width of at least a portion of at least one of the first and second connector end region is greater than the width of at least a portion of the connector medial region. The first connector end region is engaged to one turn of a first band, and the second connector end region is engaged to one turn of a second longitudinally adjacent band. The first and second bands have connected turns and unconnected turns, each connected turn having a greater width than the width of each unconnected turn.

These and other embodiments which characterize the invention are pointed out with particularity in the claims annexed hereto and forming a part hereof. However, for further understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 1:
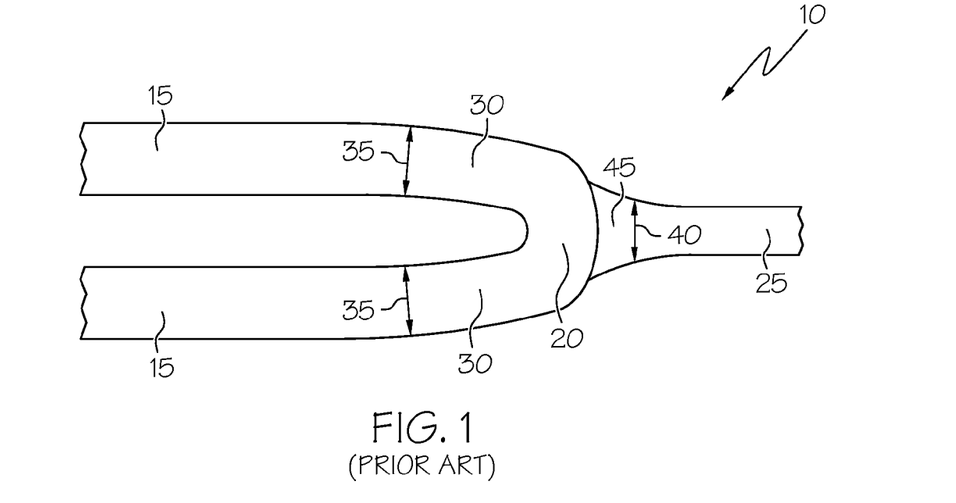
FIG. 1 (PRIOR ART) is a flat view of a portion of a prior art stent showing a connector-node combination.

Turning to the figures, a portion of a stent, shown generally at 10, with a standard connector-node combination is depicted in PRIOR ART FIG. 1. In PRIOR ART FIG. 1 two adjacent struts 15 are shown connected by a turn, or node, 20. In the present application, the terms "turn" and "node" are used interchangeably. The struts 15 have end regions 30 having a width 35, and the connector 25 has a width 40 at end region 45.

Figure 2:
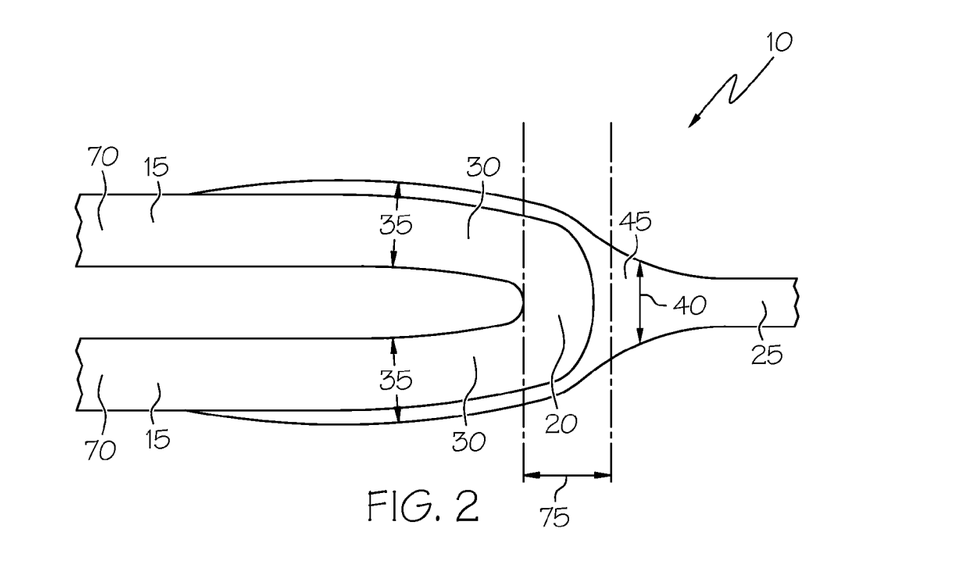
FIG. 2 is a flat view of an embodiment of the present invention, showing a portion of a stent with a durable connector-node combination.

Now referring to FIG. 2, a portion of a stent, shown generally at 10, with a new connector-node combination is depicted. In FIG. 2, the struts and connector have been configured to be wider in some portions than the struts and connectors of PRIOR ART FIG. 1. Specifically, in FIG. 2 the end regions 30 of adjacent struts 15 have a width 35 greater than the width 35 in PRIOR ART FIG. 1. Also, the width 40 of connector end region 45 is greater in the embodiment depicted in FIG. 2 than in PRIOR ART FIG. 1.

Figure 3:
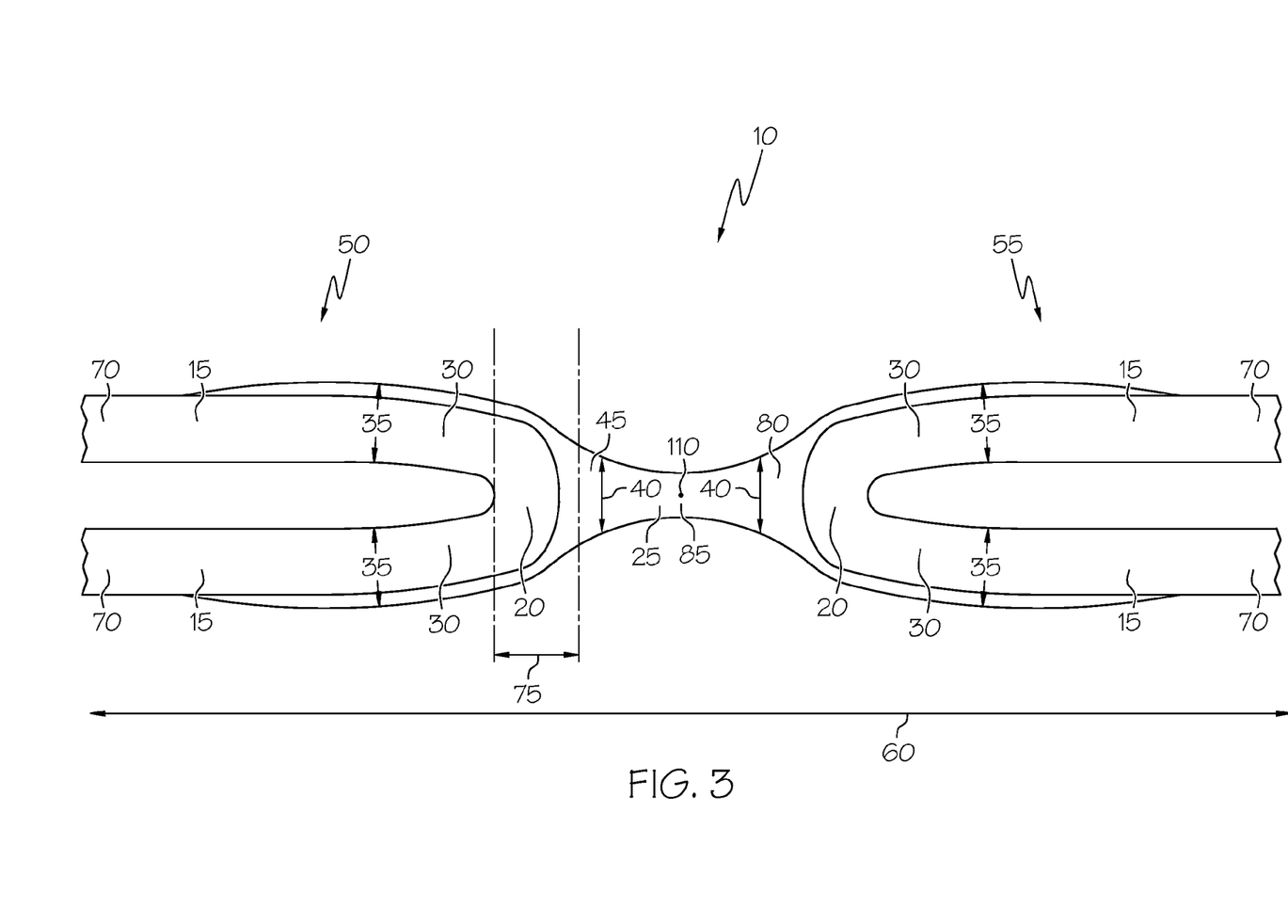
FIG. 3 is a flat view of an embodiment of the present invention, showing a portion of a stent with a connector extending between two nodes.

FIG. 3 shows the portion of the stent 10 depicted in FIG. 2 connected via connector 25 to a similar stent portion. More accurately, FIG. 3 shows a portion of a first band of stent 10, shown generally at 50, connected via connector 25 to a portion of a second band of stent 10, shown generally at 55. Bands 50 and 55 are longitudinally adjacent along a longitudinal axis 60

Figure 4:
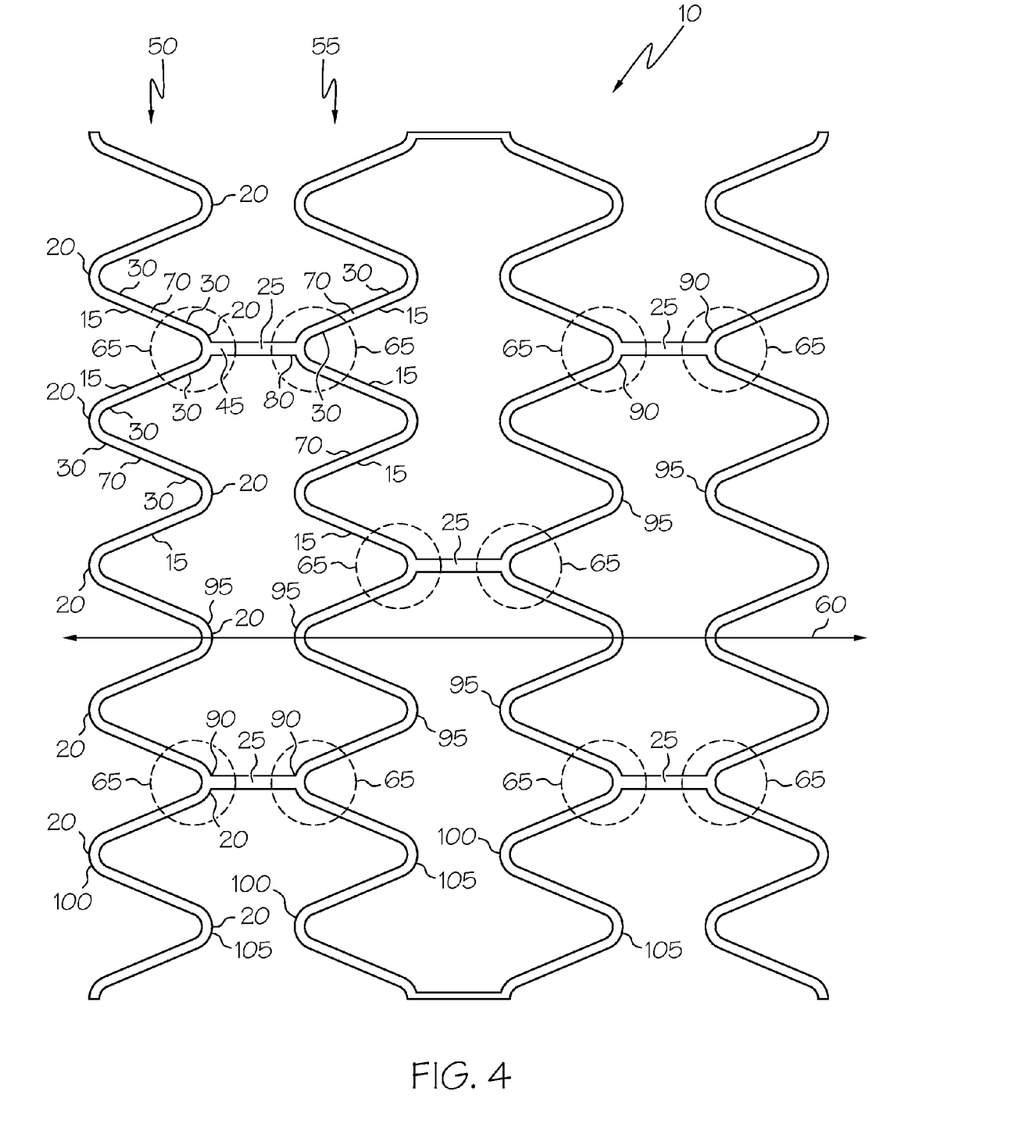
FIG. 4 is a flat view of an embodiment of the present invention, showing a portion of a stent with multiple bands engaged by connectors.

Referring now to FIG. 4, the circled regions 65 depict the portion of the stent 10 shown in FIG. 2. FIG. 4 shows the stent 10 having a plurality of longitudinally adjacent bands (50, 55) being connected by a plurality of connectors 25.

FIG. 4 shows each band (50, 55) having a plurality of interconnected struts 15. As mentioned above, and as best seen in FIGS. 2-3, each strut 15 has opposing end regions 30, a width 35, and medial region 70 located between the opposing end regions 30. FIGS. 2 and 3 also show that the width 35 of at least a portion of a strut end region 30 is greater than the width of at least a portion of the strut medial region 70 located between the strut end regions.

Within a band (50, 55) each strut end region 30 is connected to an adjacent strut end region 30 at a turn, shown generally at 20, in FIGS. 2 and 3. The turn 20 allows the struts which are connected thereto to deflect away from one another as the stent 10 is expanded. This is best seen upon comparison of FIGS. 3 and 4; FIG. 3 depicts adjacent struts 15 in a first state and FIG. 4 depicts the struts 15 being in a second state, the struts 15 in the second state being deflected substantially away from one another. The dashed lines in FIGS. 2 and 3 indicate an embodiment of a turn 20, with the boundary of the strut end regions 30 being generally the left-most dashed line, and the turn 20 with a width 75 being generally between the two dashed lines. These embodiments of the turns 20 should only be considered examples and illustrative of the concept of turns or nodes and do not preclude other embodiments and other boundaries.

Referring now to FIG. 3, each connector 25 has a first connector end region 45 and a second connector end region 80, each having a width 40. Additionally, each connector has a medial region 85 located between the connector end regions 45, 80. At least a portion of either the first connector end region 45 or the second connector end region 80, or both, is greater than the width 40 of at least a portion of the connector medial region 85. That is, the width of the connector medial region is less than at least one of the connector end regions.

As mentioned above, the connectors 25 connect longitudinally adjacent bands (50, 55). Referring now to FIG. 4, the first connector end region 45 is engaged to a turn 20 of a first band 50. The second connector end region 80 is engaged to a turn 20 of a second longitudinally adjacent band 55. First band 50 and second band 55 have connected turns 90 and unconnected turns 95. A connected turn 90 is a turn or node which is engaged to a connector 25. Conversely, an unconnected turn 95 is a turn or node which is not engaged to a connector 25.

In some embodiments, each connected turn 90 has a greater width 75 than the width of each unconnected turn 95.

In at least one embodiment, each band has a proximal end 100 and a distal end 105, as seen in FIG. 4. The proximal end 100 of a band is defined by a plurality of proximal turns 20. Likewise, the distal end 105 of a band is defined by a plurality of distal turns 20. At least one of the distal turns 20 of the first band 50 is engaged to a proximal turn 20 of the second band 55 by a connector 25.

In some embodiments, the width 40 of at least a portion of both the first connector end region 45 and the second connector end region 80 is greater than the width 40 of at least a portion of the connector medial region 85.

In at least one embodiment, the width 40 of at least a portion of the first connector end region is substantially the same as the width 40 of the second connector end region.

In some embodiments, the width 40 of at least a portion of the first connector end region is different than the width 40 of at least a portion of the second connector end region.

In some embodiments, the width 40 of at least a portion of the first connector end region is greater than the width 40 of at least a portion of the second connector end region.

In at least one embodiment, as depicted in FIG. 3, each connector 25 has a center 110, wherein the width 40 of the connector 25 is substantially symmetric about the center of the connector.

In some embodiments of the present invention, as shown in FIG. 4, each band (50, 55) has at least two connected turns 90. The two connected turns 90 are separated by a plurality of unconnected turns 95. The connected turns 90 have a greater width than the unconnected turns 95 thereby reducing the strut pair motion.

Figure 5:
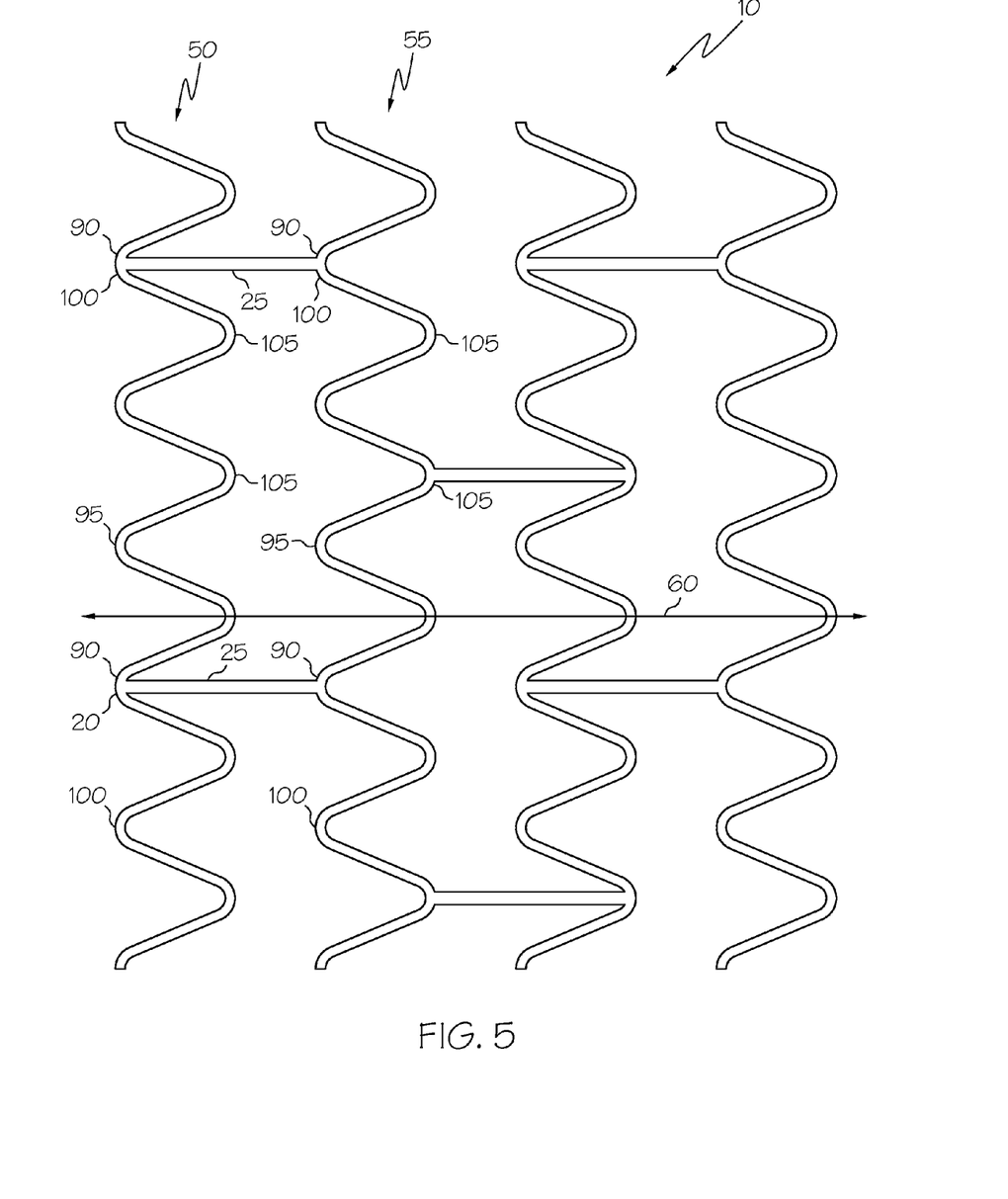
FIG. 5 is a flat view of an embodiment of the present invention, showing a portion of a stent with multiple bands engaged by connectors.
Figure 6:
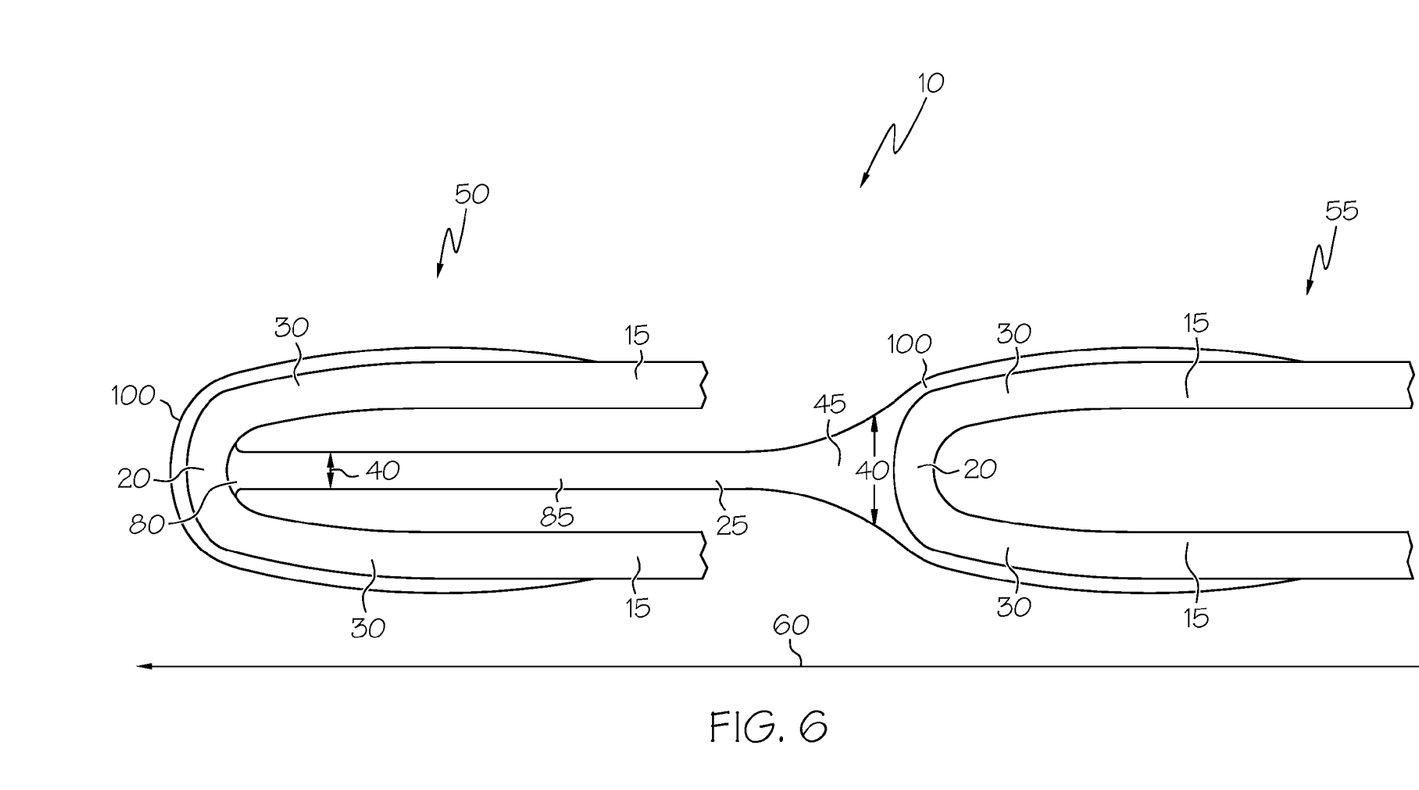
FIG. 6 is a flat view of an embodiment of the present invention, showing a portion of a stent with a connector extending between two nodes.

In some embodiments of the present invention, at least one of the proximal turns 20 of the first band 50 is engaged to a proximal turn 20 of the second band 55 by a connector 25, as seen generally in FIG. 5 and in more detail in FIG. 6. In the embodiment shown in FIG. 6, the width 40 of a portion of the first connector end region 45 is greater than the width 40 of a portion of the second connector end region 80. As seen in FIG. 6, the connector 25 gradually tapers from the end region 45 to the end region 80.

In some embodiments (not depicted), the connector 25 tapers the opposite direction such that the width 40 of the first connector end region 45 is less than the width 40 of the second connector end region 80. In some embodiments, the connector 25 does not taper between the end regions.

Figure 7:
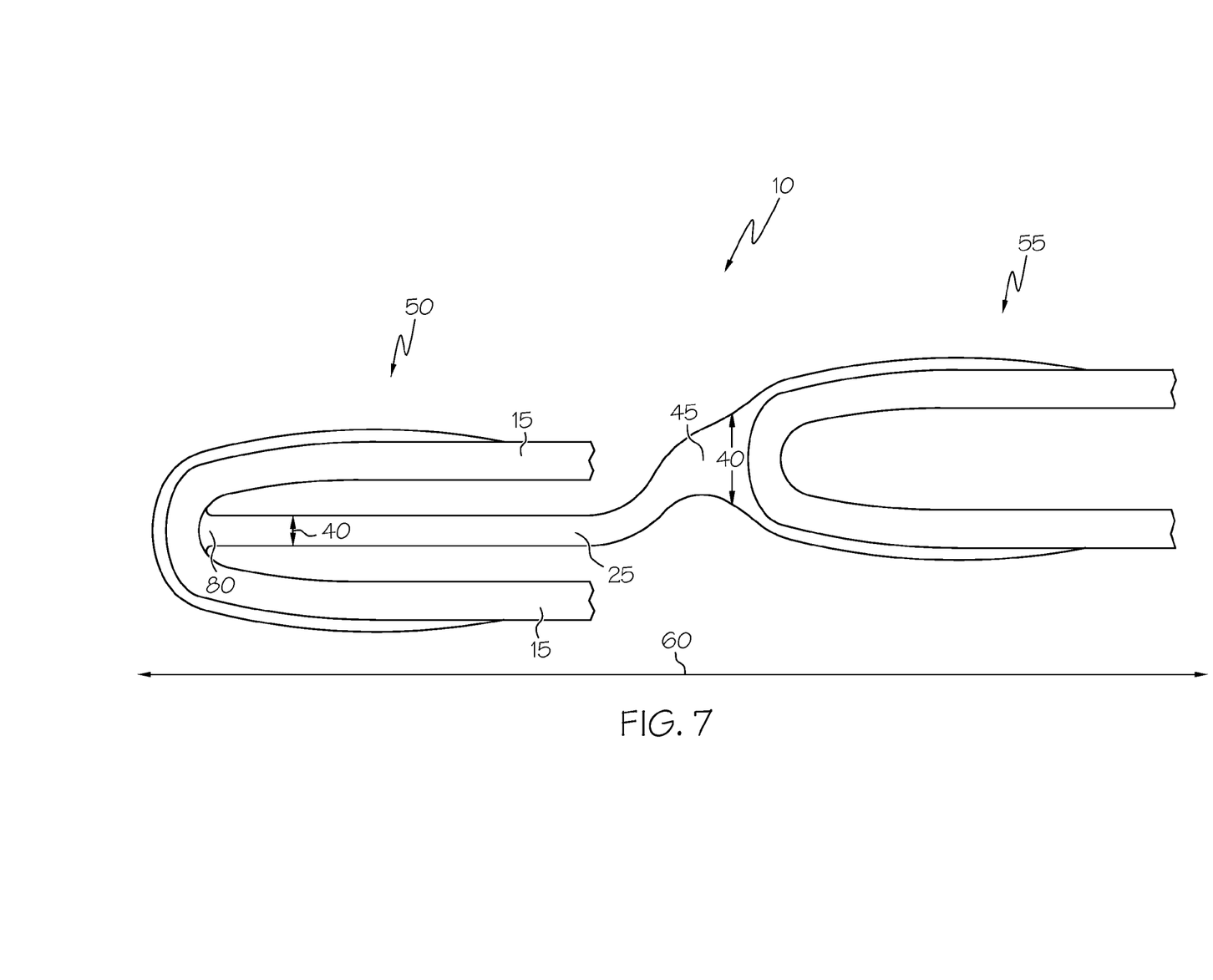
FIG. 7 is a flat view of an embodiment of the present invention, showing a portion of a stent with a connector extending between two nodes.

In at least one embodiment of the present invention, the stent includes a longitudinal axis 60, wherein at least one of the first connector end region 45 and second connector end region 80 are substantially parallel to the longitudinal axis 60, as depicted in FIG. 7.

In some embodiments, the stent includes a longitudinal axis 60, wherein both the first connector end region 45 and second connector end region 80 are substantially parallel to the longitudinal axis 60, as depicted in FIGS. 5 and 6.

Figure 8:
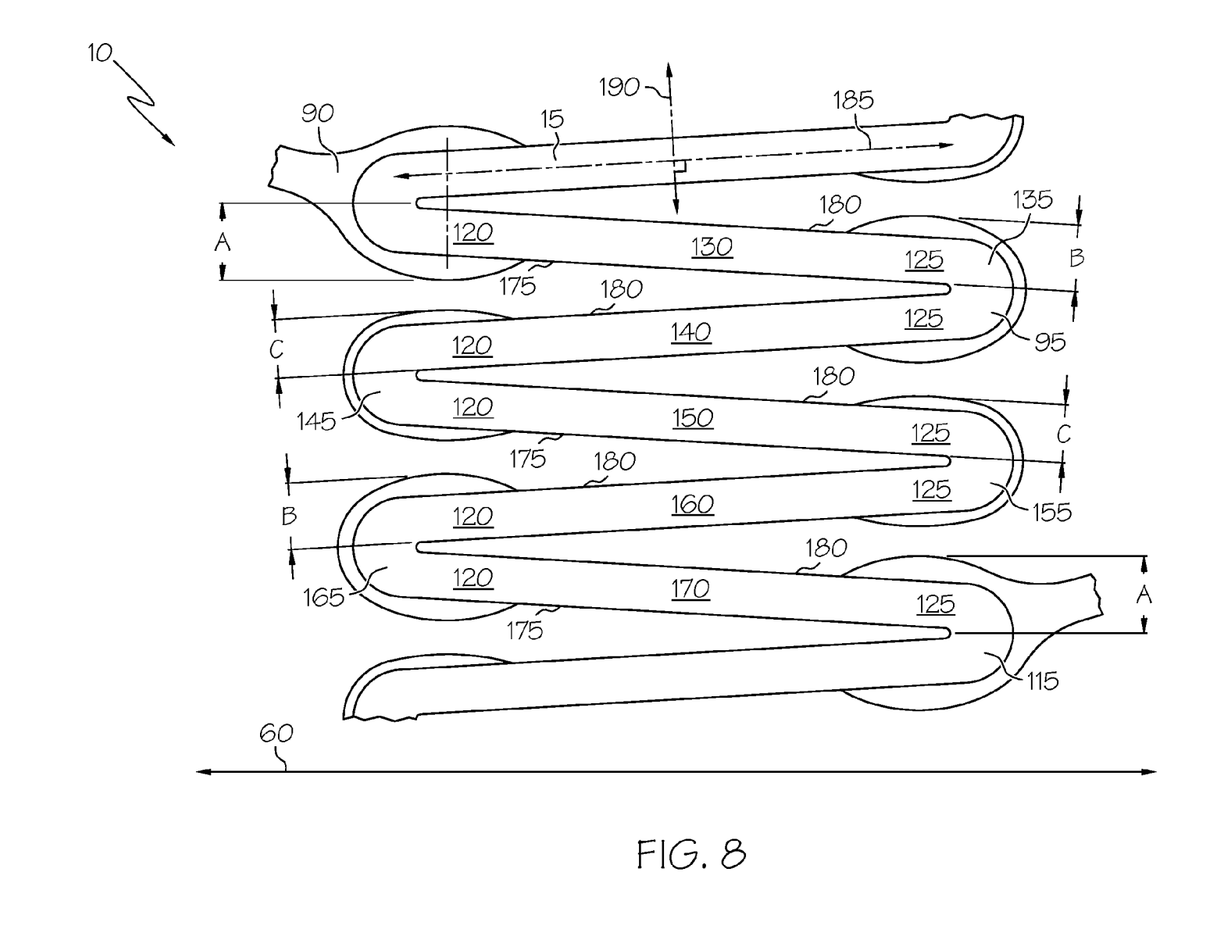
FIG. 8 is a flat view of an embodiment of the present invention, showing connected and unconnected nodes of a band of a stent.

Referring now to FIG. 8, at least one band has at least two connected turns (90, 115). The first connected turn 90 and the second connected turn 115 are separated by four unconnected turns 95. As described earlier, the opposing strut end regions include a proximal end region 120 and a distal end region 125.

As seen in FIG. 8, the struts and turns are interconnected to form an alternating pattern. Specifically, the proximal end region 120 of the first strut 130 is engaged to the first connected turn 90, and the distal end region 125 of the first strut 130 is engaged to the first unconnected turn 135. The distal end region 125 of the second strut 140 is also engaged to the first unconnected turn 135, and the proximal end region 120 of the second strut 140 is engaged to the second unconnected turn 145.

Next, the proximal end region 120 of the third strut 150 is engaged to the second unconnected turn 145, and the distal end region 125 of the third strut 150 is engaged to the third unconnected turn 155. The distal end region 125 of the fourth strut 160 is also engaged to the third unconnected turn 155, and the proximal end region 120 of the fourth strut 160 is engaged to the fourth unconnected turn 165.

Finally, the proximal end region 120 of the fifth strut 170 is engaged to the fourth unconnected turn 165, and the distal end region 125 of the fifth strut 170 is engaged to the second connected turn 115.

As further seen in FIG. 8, the width "A" of the proximal end region 120 of the first strut 130 is greater than the width "B" of the distal end region 125 of the first strut 130. Also, the width of the distal end region 125 of the second strut 140 is greater than the width "C" of the proximal end region 120 of the second strut 140. Thus width "A" is greater than width "B", and width "B" is greater than width "C".

This pattern is reversed as the band continues toward the second connected turn 115. In particular, the width "C" of the distal end region 125 of the fourth strut 160 is less than the width "B" of the proximal end region 120 of the fourth strut 160. Also, the width of the proximal end region 120 of the fifth strut 170 is less than the width "A" of the distal end region 125 of the second unconnected strut 115.

In at least one embodiment, the widths of both strut end regions engaged to a turn are substantially equal. For example, in FIG. 8 the distal end region 125 of the first strut 130 and the second strut 140 are both substantially equal to "B", and the proximal end region 120 of the second strut 140 and the third strut 150 are both substantially equal to "C". The distal end regions engaged to the third unconnected turn 155 and the proximal end regions engaged to the fourth unconnected turn 165 can also be similarly constructed.

As one of skill in the art would recognize, the embodiment depicted in FIG. 8 may be generalized to include a plurality N, where N is an integer, of unconnected turns between the connected turns. In such a generalized embodiment, like above, after the first connected turn, the proximal and distal end regions of the struts will decrease in width until the N/2 turn at which point they increase in width as they approach the second connected turn.

Still referring to FIG. 8, each strut has a first side 175, a second side 180, a longitudinal axis 185, and a transverse axis 190 which is perpendicular to the strut's longitudinal axis 185. In some embodiments, like the one depicted in FIG. 8, portions of the end regions bulge outwardly. And, as seen, these bulged portions extend outwardly from the first side at one end region, and then outwardly from the second side at the opposing end region.

In particular, at the proximal end region 120 of the first strut 130, the first side 175 extends outwardly along a transverse axis 190 more than the second side 180, and at the distal end region 125 of the first strut 130, the second side 180 extends outwardly along a transverse axis 190 more than the first side 175.

Similarly, at the proximal end region 120 of the second strut 140, the second side 180 extends outwardly along a transverse axis 190 more than the first side 175, and at the distal end region 125 of the second strut 140, the first side 175 extends outwardly along a transverse axis 190 more than the second side 180.

Looking at the third strut 150, at the proximal end region 120, the first side 175 extends outwardly along a transverse axis 190 more than the second side 180, and at the distal end region 125 of the third strut 150, the second side 180 extends outwardly along a transverse axis 190 more than the first side 175.

At the proximal end region 120 of the fourth strut 160, the second side 180 extends outwardly along a transverse axis 190 more than the first side 175, and at the distal end region 125 of the second strut 140, the first side 175 extends outwardly along a transverse axis 190 more than the second side 180.

Looking at the fifth strut 170, at the proximal end region 120, the first side 175 extends outwardly along a transverse axis 190 more than the second side 180, and at the distal end region 125 of the fifth strut 170, the second side 180 extends outwardly along a transverse axis 190 more than the first side 175.

In some embodiments of the present invention, the stent is comprised of a shape-memory material such nitinol.

In at least one embodiment, the stent is comprised of a nickel-titanium-platinum alloy.

In some embodiments, the stent is comprised of stainless steel.

In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments the at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the alternate embodiments of the invention. Those skilled in the art may recognize other equivalents to the specific embodiment described herein which equivalents are intended to be encompassed by the claims attached hereto.

What is claimed is:

1. A stent comprising:
   a plurality of longitudinally adjacent bands, the longitudinally adjacent bands being connected by a plurality of connectors,
   each band comprising a plurality of interconnected struts, each strut having a strut width, each strut further having opposing strut end regions and a strut medial region, the width of at least a portion of a strut end region being greater than the width of at least a portion of the strut medial region, within a band each strut end region being connected to an adjacent strut end region at a turn, each turn having a turn width,
   each connector having a connector width, each connector further having a first connector end region, a second connector end region and a connector medial region therebetween, the width of at least a portion of at least one of the first connector end region and second connector end region being greater than the width of at least a portion of the connector medial region,
   the first connector end region engaged to one turn of a first band and the second connector end region engaged to one turn of a second longitudinally adjacent band, the first and second bands having connected turns and unconnected turns, each connected turn having a greater width than the width of each unconnected turn.

2. The stent of claim 1, wherein each band has a proximal end and a distal end, the proximal end being defined by a plurality of proximal turns, the distal end being defined by a plurality of distal turns, at least one of the distal turns of the first band being engaged to a proximal turn of the second band by a connector.

3. The stent of claim 2, wherein the width of at least a portion of both the first connector end region and the second connector end region is greater than the width of at least a portion of the connector medial region.

4. The stent of claim 3, each connector further having a center, wherein the width of the connector is substantially symmetric about the center of the connector.

5. The stent of claim 3, wherein each band has at least two connected turns, the at least two connected turns being separated by a plurality of unconnected turns.

6. The stent of claim 1, wherein each band has a proximal end and a distal end, the proximal end being defined by a plurality of proximal turns, the distal end being defined by a plurality of distal turns, at least one of the proximal turns of the first band being engaged to a proximal turn of the second band by a connector.

7. The stent of claim 6, wherein the width of at least a portion of the first connector end region is greater than the width of at least a portion of the second connector end region.

8. The stent of claim 1, the stent further comprising a longitudinal axis, wherein at least one of the first connector end region and second connector end region are substantially parallel to the longitudinal axis.

9. The stent of claim 1, the stent further comprising a longitudinal axis, wherein both the first connector end region and second connector end region are substantially parallel to the longitudinal axis.

10. The stent of claim 1, wherein at least one band comprises at least a first connected turn and a second connected turn, the first connected turn and second connected turn being separated by four unconnected turns, and wherein the opposing end regions comprise a proximal end region and a distal end region,
    wherein the proximal end region of a first strut is engaged to the first connected turn and the distal end region of the first strut is engaged to a first unconnected turn, the width of the proximal end region of the first strut being greater than the width of the distal end region of the first strut, and
    wherein the distal end region of a second strut is engaged to the first unconnected turn and the proximal end region of the second strut is engaged to a second unconnected turn, the width of the distal end region of the second strut being greater than the width of the proximal end region of the second strut, and
    wherein the proximal end region of a third strut is engaged to the second unconnected turn and the distal end region of the third strut is engaged to a third unconnected turn, the width of the proximal end region of the third strut being substantially equal to the width of the distal end region of the third strut, and
    wherein the distal end region of a fourth strut is engaged to the third unconnected turn and the proximal end region of the third strut is engaged to a fourth unconnected turn, the width of the distal end region of the fourth strut being less than the width of the proximal end region of the fourth strut, and
    wherein the proximal end region of a fifth strut is engaged to the fourth unconnected turn and the distal end region of the fifth strut is engaged to the second connected turn, the width of the proximal end region of the fifth strut being less than the width of the distal end region of the fifth strut.

11. The stent in claim 10, wherein the width of the distal end region of the first strut and the width of the distal end region of the second strut are substantially equal, and
    wherein the width of the proximal end region of the second strut and the width of the proximal end region of the third strut are substantially equal, and
    wherein the width of the distal end region of the third strut and the width of the distal end region of the fourth strut are substantially equal, and
    wherein the width of the proximal end region of the fourth strut and the width of the proximal end region of the fifth strut are substantially equal.

12. The stent in claim 10, wherein each of the first, second, third, fourth, and fifth struts have a first side, a second side, and a longitudinal axis, and wherein the first side extends outwardly from the longitudinal axis along a transverse axis more than the second side at the proximal end region of the first strut, and the second side extends outwardly from the longitudinal axis along a transverse axis more than the first side at the distal end region of the first strut, and wherein the first side extends outwardly from the longitudinal axis along a transverse axis more than the second side at the distal end region of the second strut, and the second side extends outwardly from the longitudinal axis along a transverse axis more than the first side at the proximal end region of the first strut, and wherein the first side extends outwardly from the longitudinal axis along a transverse axis more than the second side at the proximal end region of the third strut, and the second side extends outwardly from the longitudinal axis along a transverse axis more than the first side at the distal end region of the third strut, and wherein the first side extends outwardly from the longitudinal axis along a transverse axis more than the second side at the distal end region of the fourth strut, and the second side extends outwardly from the longitudinal axis along a transverse axis more than the first side at the proximal end region of the fourth strut, and wherein the first side extends outwardly from the longitudinal axis along a transverse axis more than the second side at the proximal end region of the fifth strut, and the second side extends outwardly from the longitudinal axis along a transverse axis more than the first side at the distal end region of the fifth strut.

13. The stent of claim 1, wherein the stent is comprised of a nickel-titanium-platinum alloy.

14. The stent of claim 1, wherein the stent is comprised of stainless steel.

\* \* \* \* \*